United States Patent
Chen

(10) Patent No.: US 11,628,210 B2
(45) Date of Patent: Apr. 18, 2023

(54) CHIMERIC ANTIGEN RECEPTORS THAT BIND TO SSEA4 AND USES THEREOF

(71) Applicant: CHO Pharma USA, Inc., Woburn, MA (US)

(72) Inventor: Lan Bo Chen, Lexington, MA (US)

(73) Assignee: CHO Pharma USA, Inc., Woburn, MA (US)

( * ) Notice: Subject to any disclaimer, the term of this patent is extended or adjusted under 35 U.S.C. 154(b) by 444 days.

(21) Appl. No.: 16/931,676

(22) Filed: Jul. 17, 2020

(65) Prior Publication Data

US 2020/0338177 A1 Oct. 29, 2020

Related U.S. Application Data

(62) Division of application No. 15/926,382, filed on Mar. 20, 2018, now Pat. No. 10,751,399.

(51) Int. Cl.
| | | |
|---|---|---|
| *A61K 39/00* | (2006.01) | |
| *C07K 14/705* | (2006.01) | |
| *C07K 14/725* | (2006.01) | |
| *C07K 14/71* | (2006.01) | |
| *A61P 35/00* | (2006.01) | |
| *C07K 16/18* | (2006.01) | |

(52) U.S. Cl.
CPC .......... *A61K 39/0011* (2013.01); *A61P 35/00* (2018.01); *C07K 14/7051* (2013.01); *C07K 14/70517* (2013.01); *C07K 14/70578* (2013.01); *C07K 14/71* (2013.01); *C07K 16/18* (2013.01); *A61K 2039/5156* (2013.01); *A61K 2039/5158* (2013.01); *C07K 2317/622* (2013.01); *C07K 2319/00* (2013.01)

(58) Field of Classification Search
CPC combination set(s) only.
See application file for complete search history.

(56) References Cited

U.S. PATENT DOCUMENTS

| | | |
|---|---|---|
| 2014/0271635 A1 | 9/2014 | Brogdon et al. |
| 2016/0102151 A1 | 4/2016 | Wong et al. |
| 2016/0185861 A1 | 6/2016 | Bedoya et al. |
| 2017/0283489 A1 | 10/2017 | Bosio et al. |
| 2018/0028631 A1* | 2/2018 | Chen ............... C07K 14/70521 |
| 2018/0028633 A1 | 2/2018 | Chen |

FOREIGN PATENT DOCUMENTS

| | | |
|---|---|---|
| CN | 107188968 A | 9/2017 |
| WO | WO-2016/026742 A1 | 2/2016 |

OTHER PUBLICATIONS

Dai et al "Chimeric Antigen Receptors Modified T-Cells for Cancer Therapy" Journal of the National Cancer Institute vol. 108, pp. 1-14, 2016.

Han et al "Chimeric Antigen Receptor-Engineered T Cells for Cancer Immunotherapy: Progress and Challenges" Journal of Hematology and Oncology vol. 6, pp. 1-7, 2013.
Harichandan et al "Isolation of Adult Human Spermatogonial Progenitors Using Novel Markers" Journal of Molecular Cell Biology vol. 5, pp. 351-353, 2013.
He et al "Knock-In of Large Receptor Genes in Human Cells Via CRISPR/Cas9-Induced Homology-Dependent and Independent DNA Repair" Nucleic Acids Research vol. 44, pp. 1-14, 2016.
Jin et al "Safe Engineering of CAR T Cells for Adoptive Cell Therapy of Cancer Using Long-Term Episomal Gene Transfer" Molecular Medicine vol. 8, pp. 702-711, 2016.
Kaiser et al "Towards a Commercial Process for the Manufacture of Genetically Modified T Cells for Therapy" Cancer Gene Therapy vol. 22, pp. 72-78, 2015.
Kim et al "Cancer Stem Cell Surface Markers on Normal Stem Cells" BMB Reports vol. 50, pp. 285-298, 2017.
Liechtenstein et al "Lentiviral Vectors for Cancer Immunotherapy and Clinical Applications" Cancers vol. 5, pp. 815-837, 2013.
Lou et al "Stage-Specific Embryonic Antigen-4 as a Potential Therapeutic Target in Glioblastoma Multiforme and Other Cancers" PNAS vol. 111, pp. 2482-2487, 2014.
Maher "Clinical Immunotherapy of B-Cell Malignancy Using CD19-Targeted Car T-Cells" Current Gene Therapy vol. 14, pp. 35-43, 2014.
Maiti et al "Sleeping Beauty System to Redirect T-Cell Specificity for Human Applications" Journal of Immunotherapy, 2013.
Miura et al "Easi-CRSIPR for Creating Knock-In and Conditional Knockout Mouse Models Using Long ssDNA Donors" Nature Protocols vol. 13, pp. 195-215, 2018.
Nakazawa et al "PiggyBac-Mediated Cancer Immunotherapy Using EBV-Specific Cytotoxic T-Cells Expressing HER2-Specific Chimeric Antigen Receptor" Molecular Therapy vol. 19, pp. 2133-2143, 2011.
Pfeifer et al "Sialyl Glycolipid Stage-Specific Embryonic Antigen 4 (SSEA4)—A Novel Target for CAR T Cell Therapy of Solid Cancers" Molecular Therapy vol. 24, pp. S259, 2016.
Schonfeld et al "Selective Inhibition of Tumor Growth by Clonal NK Cells Expressing an ErbB2/HER2-Specific Chimeric Antigen Receptor" Molecular Therapy vol. 23, pp. 330-338, 2015.

(Continued)

*Primary Examiner* — Brad Duffy
*Assistant Examiner* — Shireen Attaran
(74) *Attorney, Agent, or Firm* — Cesari & McKenna, LLP

(57) ABSTRACT

An isolated nucleic acid that contains a nucleotide sequence that encodes the polypeptide of SEQ ID NO: 3. The polypeptide of SEQ ID NO: 3 specifically binds to stage-specific embryonic antigen 4 (SSEA4). Also disclosed is a recombinant cell comprising the isolated nucleic acid described above, a viral vector containing the above isolated nucleic acid, and an isolated polypeptide including the sequence of SEQ ID NO: 3. Provided as well is a chimeric antigen receptor (CAR) that includes a single chain Fv having the sequence of SEQ ID NO: 3 and specifically binding to SSEA4. Moreover, a method is disclosed for treating a tumor by transducing in vitro the T cells of a subject having a tumor expressing SSEA4 with a vector that encodes the CAR, expanding the transduced T cells, and infusing the expanded transduced T cells into the subject, whereby an anti-tumor T cell response is raised.

6 Claims, 2 Drawing Sheets

Specification includes a Sequence Listing.

(56) References Cited

OTHER PUBLICATIONS

Sivasubramaniyan et al "Expression of Stage-Specific Embryonic Antigen-4 (SSEA-4) Defines Spontaneous Loss of Epithelial Phenotype in Human Solid Tumor Cells" Glycobiology vol. 25, pp. 902-917, 2015.

Wang et al "A Long Way to the Battlefront: CAR T Cell Therapy Against Solid Cancers" Journal of Cancer vol. 10, pp. 3112-3123, 2019.

Yan et al "Critical Factors in Chimeric Antigen Receptor-Modified T-Cell (CAR-T) Therapy for Solid Tumors" OncoTargets and Therapy vol. 12, pp. 193-204, 2019.

Eller, et al. Affinity of monoclonal antibodies for Globo-series glycans. Carbohydrate Research 2014. pp. 1-6. vol. 397.

Pfeifer, et al. Sialyl Glycolipid Stage-Specific Embryonic Antigen 4 (SSEA4)—A Novel Target for CAR T Cell Therapy of Solid Cancers. Molecular Therapy 2016. p. S259. vol. 4, No. 1.

Posey, et al. 586. Precise Glycoediting by CRISPR/Cas9-Meditated Gene Disruption Elucidates the Specificity of a Chimeric Antigen Receptor for the Globoside SSEA-4. Molecular Therapy: The Journal of the American Society of Gene Therapy; 20th Annual Meeting of the American-Society-of-Gene-and-Cell Therapy (ASGCT) 2017. p. 271. vol. 25, No. 5, Suppl. 1.

\* cited by examiner

CHIMERIC ANTIGEN RECEPTORS THAT BIND TO SSEA4 AND USES THEREOF

CROSS-REFERENCE TO RELATED APPLICATIONS

The present application is a divisional of copending U.S. patent application Ser. No. 15/926,382, which was filed on Mar. 20, 2018. The content of the prior application is hereby incorporated by reference in its entirety.

BACKGROUND

Targeted cancer immunotherapy, as compared to chemotherapy, holds the promise of not only better efficacy, both short-term and long-term, but also fewer side effects.

For example, anti-cancer vaccines targeting a tumor-specific carbohydrate antigen, e.g., Globo H, stage-specific embryonic antigen 3 ("SSEA3"), and stage-specific embryonic antigen 4 ("SSEA4") have been developed to stimulate a patient's own immune system to develop antibodies against these antigens, which leads to antibody-dependent cellular cytotoxicity, antibody-dependent phagocytosis, complement-dependent cell lysis, as well as direct cytostatic and/or cytotoxic effects.

Such an approach often loses effectiveness over time as a result of an inhibitory environment in the tumor. The inhibitory environment blocks one or all of antibodies, NK cells, macrophages, and complement from entering the tumor.

Recently, chimeric antigen receptors ("CARs") have been developed to obviate the drawbacks mentioned above. A CAR contains (i) an extracellular domain that binds to the tumor antigen and (ii) one or more intracellular domains that provide both primary and co-stimulatory signals to the T cells. T cells can be engineered in vitro to express CAR having an extracellular domain of choice.

The CAR approach has proven to be effective, yet not without serious side effects. For example, activation of a large number of T cells expressing CAR causes cytokine release syndrome. This syndrome, characterized by high fever, hypotension, and hypoxia, can result in multi-organ failure and even death.

There is a need to develop CAR-based tumor therapies that are safer and more effective than those currently in use.

SUMMARY

To meet the need discussed above, an isolated nucleic acid is disclosed that contains a nucleotide sequence that encodes the polypeptide of SEQ ID NO: 3. The polypeptide of SEQ ID NO: 3 specifically binds to stage-specific embryonic antigen 4 (SSEA4).

Also disclosed is a recombinant cell comprising the isolated nucleic acid described above, where the recombinant cell expresses the polypeptide of SEQ ID NO: 2.

Further, a viral vector containing the above isolated nucleic acid is within the scope of the invention. The viral vector is a lentiviral vector, a gamma-retroviral vector, or an adeno-associated viral vector.

Moreover, an isolated polypeptide including the sequence of SEQ ID NO: 3, Again, the isolated polypeptide specifically binds to SSEA4.

Provided as well is a chimeric antigen receptor (CAR) that includes a single chain Fv (scFv) having the sequence of SEQ ID NO: 3 and specifically binding to SSEA4, and a first endodomain from CD3ζ or FcεRIγ.

Finally, a method is disclosed for treating a tumor in a subject, the method including the steps of (i) obtaining T cells from a subject having a tumor; (ii) transducing the T cells in vitro with a vector that contains a nucleic acid encoding a CAR including a scFv that specifically recognizes SSEA-4, whereby the transduced T cells express the CAR; (iii) expanding the transduced T cells in vitro; and (iv) infusing the expanded transduced T cells into the subject having a tumor, whereby an anti-tumor T cell response is raised. The scFv has the amino acid sequence of SEQ ID NO: 3 and cells in the tumor express SSEA4.

The details of one or more embodiments of the invention are set forth in the description and drawings below. Other features, objects, and advantages of the invention will be apparent from the description and from the claims.

BRIEF DESCRIPTION OF THE DRAWINGS

The description below refers to the accompanying drawings, of which.

DETAILED DESCRIPTION

Figure 1:
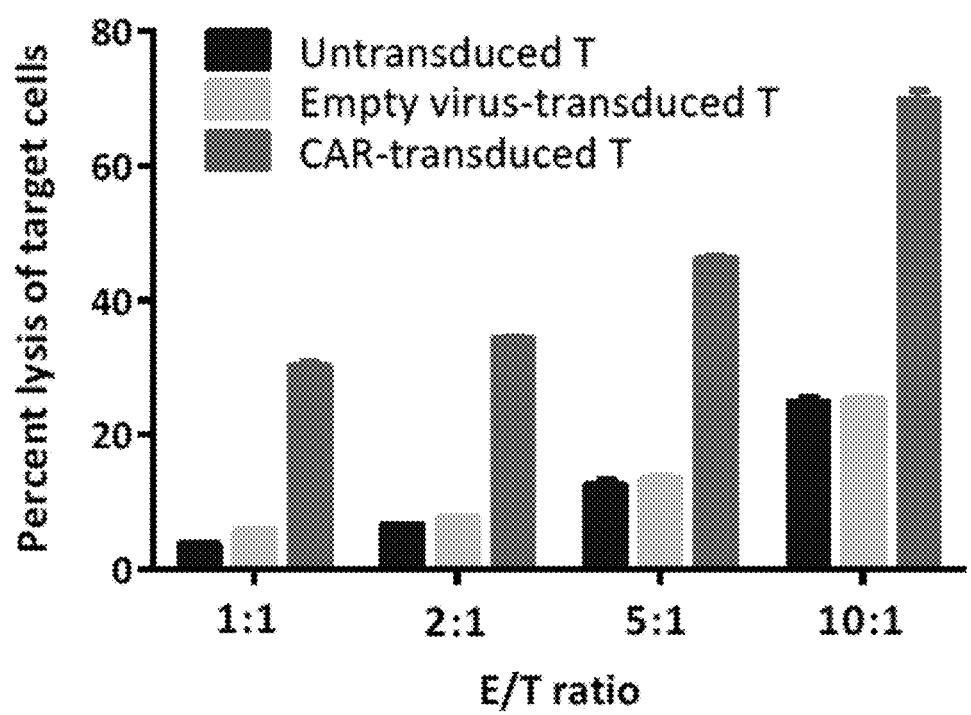
FIG. 1 is a bar graph of percent lysis of target cells by the indicated effector T cells at different effector to target ratios.

As mentioned above, to meet the need to develop CAR-based tumor therapies, an isolated nucleic acid is provided that includes a nucleotide sequence encoding the polypeptide of SEQ ID NO: 3. The polypeptide of SEQ ID NO: 3 is an scFv that specifically binds to SSEA4. In a particular example, the isolated nucleic acid has the nucleotide sequence of SEQ ID NO: 1.

Also within the scope of the invention is a recombinant cell that contains the isolated nucleic acid having the nucleotide sequence of SEQ ID NO: 1. The recombinant cell expresses the polypeptide of SEQ ID NO: 2, i.e., a CAR construct that includes the scFv of SEQ ID NO: 3. The recombinant cell can be a T cell, e.g., a $CD4^+$ or $CD8^+$ T cell. Other cells that can be used include NK, iNKT, monocytes, macrophages, microglia, dendritic cells, and neutrophils.

The isolated nucleic acid that includes a nucleotide sequence encoding the polypeptide of SEQ ID NO: 3, e.g., a CAR construct, can be contained within a viral vector.

Exemplary viral vectors include a lentiviral vector, a gamma-retroviral vector, and an adeno-associated viral vector. Viral vectors based on lentivirus or gamma retroviruses are set forth in Dai et al. 2016, J. Natl. Cancer Inst. 108:1-14 ("Dai et al."); Jin et al. 2016, EMBO Mol. Med. 8:702-711; Liechtenstein et al. 2013, Cancers 5:815-837; and Schonfeld et al. 2015, Mol. Therapy 23:330-338. Such viral vectors are used for integrating the CAR-encoding nucleic acid into T cell genomic DNA to produce stable expression of the CAR.

In a particular example, the viral vector is a lentiviral vector that includes the nucleotide sequence of SEQ ID NO: 1.

Alternatively, the CAR construct can be included in a vector that contains sequences to facilitate transposon-mediated genomic integration into T cells of the CAR-encoding nucleic acid, e.g., SEQ ID NO: 1. Examples of these expression vectors are the so-called "PiggyBac" and "Sleeping Beauty" expression vectors. See Nakazawa et al. 2011, Mol. Ther. 19:2133-2143 and Maiti et al. 2013, J. Immunotherapy 36:112-123.

In yet another alternative, a vector containing the CAR construct also contains genomic nucleic acid sequences flanking the CAR construct that allow for clustered regularly interspaced short palindromic repeat (CRISPR)-mediated insertion of the CAR construct into the genome of the T cells. Examples of CRISPR constructs for inserting the CAR into the genome can be found, e.g., in Miura et al. 2018, Nature Protocols 13:195-215 and He et al. 2016, Nucl. Acids Res. 44:1-14.

Further disclosed is an isolated polypeptide containing the sequence of SEQ ID NO: 3. The isolated polypeptide, an scFv, specifically binds to SSEA-4.

Additionally provided is a CAR that includes an scFv that specifically binds to stage-specific embryonic antigen 4. The scFv can have the sequence of SEQ ID NO: 3. The CAR further includes a first endodomain from CD3ζ or FcεRIγ. In an exemplary CAR, the first endodomain is from CD3ζ.

The CAR can also contain a second endodomain. The second endodomain can be, but is not limited to, an endodomain from CD28, CD137, CD4, OX40, and ICOS. If a second endodomain is present in the CAR, the scFv is fused to the second endodomain and the second endodomain is fused to the first endodomain. A particular example of a CAR has a second endodomain from CD137. In another specific example, the CAR has the amino acid sequence of SEQ ID NO: 4.

As mentioned above, a tumor-treating method is provided including, among others, the step of obtaining T cells from a subject having a tumor and the step of transducing the T cells in vitro with a vector that contains a nucleic acid encoding a CAR including a scFv that specifically recognizes SSEA4.

Procedures for obtaining T cells are known in the art. See, e.g., Kaiser et al. 2015, Cancer Gene Therapy 22:72-78 ("Kaiser et al."). The T cells can be CD4+, CD8+, or NK cells. In an exemplary method, CD8+ cells are obtained from the subject.

The T cells are transduced in vitro with the CAR vector described above. Transduction of T cells can be performed by electroporation, lipofection, lentiviral infection, gamma retrovirus infection, or adeno-associated virus infection, depending upon the type of CAR vector employed.

More specifically, if the CAR vector is a PiggyBac, Sleeping Beauty, or CRISPR-based expression vector, it can be transduced into the T cells via electroporation or lipofection. A CRISPR-base expression vector is co-transfected with a vector that expresses a guide RNA complementary to a sequence adjacent to a protospacer adjacent motif at an intended genomic insertion site in the T cells.

If the CAR vector is viral-based, virus particles are prepared and used to infect T cells.

The tumor treatment method also includes the step of expanding the transduced T cells in vitro and the step of infusing the expanded transduced T cells into the subject having a tumor.

Transduced T cells are expanded in vitro, using methods known in the art. See Kaiser et al. The expanded T cells are then infused in one batch or in two or more batches into the subject having a tumor.

In a specific alternative of the tumor-treating method, the method further includes a preconditioning step that is performed prior to the just-mentioned infusion step. The preconditioning step is accomplished by treating the subject with a drug that induces lymphodepletion. Examples of these drugs include cyclophosphamide and fludarabine. Additional drug examples can be found in Dai et al. and Han et al. 2013, J. Hematol. Oncol. 6:47-53.

In the tumor-treating method, the transduced T cells can further express the polypeptide of SEQ ID NO: 5, i.e., an epidermal growth factor receptor t domain III-IV (EGFRt), in addition to the CAR. In this way, the infused expanded T cells can be deleted in vivo with an anti-epidermal growth factor receptor antibody that binds to EGFRt. For example, cetuximab is administered to the subject to kill infused T cells in vivo. An exemplary nucleic acid that encodes the CAR together with EGFRt has the nucleic acid sequence of SEQ ID NO: 1.

The method set forth above can be used for treating a tumor that contains cells expressing SSEA4. The tumors that can be treated include, but are not limited to breast, colon, gastrointestinal, kidney, lung, liver, ovarian, pancreatic, rectal, stomach, testicular, thymic, cervical, prostate, bladder, skin, nasopharyngeal, esophageal, oral, head and neck, bone, cartilage, muscle, lymph node, bone marrow, and brain tumors.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever. All publications and patent documents cited herein are incorporated by reference in their entirety.

EXAMPLES

Example 1: Production of a Lentivirus Containing an Anti-SSEA4 CAR Construct Construction of Lentiviral Vector Encoding an Anti-SSEA4 CAR A lentiviral construct was prepared in *E. coli* using standard recombinant DNA techniques and verified by DNA sequencing. More specifically, a nucleic acid encoding an scFv having the sequence of SEQ ID NO: 3 was cloned into a lentiviral plasmid vector downstream of an EF-1 alpha promoter and a signal peptide encoding sequence and upstream of a CD8 hinge-encoding sequence to create a CAR cassette. The CAR cassette also encodes a CD8 transmembrane domain, a CD137 intracellular signaling domain, a CD3ζ endodomain, a *Thosea asigna* self-cleaving peptide T2A, and an EGFRt domain III-IV. The CAR cassette has the nucleic acid sequence of SEQ ID NO: 1. The lentiviral plasmid vector contains additional sequences to facilitate production of lentivirus particles.

Lentivirus Packaging and Production

Packaging and production of lentiviruses was performed using established techniques. Packaging cells, i.e., 293T cells, were plated at $5\times10^6$ cells in 10 mL of a complete culture medium in a 10 cm culture dish. The cells were incubated overnight at 37° C. in 5% CO2. A transfection complex was prepared by combining in PBS a transfection reagent, the lentiviral vector described above, a packaging vector, and an envelope vector. The transfection complex was added to the culture dish containing the packaging cells and the cells incubated for 6 to 8 h at 37° C. in 5% CO2. The medium was replaced and the cells incubated for 24 h. The culture medium was collected and replaced with fresh medium. This 24 h incubation and medium collection was repeated twice. All of the collected medium was combined and passed through a 0.45 μm filter. The filtrate was centrifuged at 50,000×g for 2 h to pellet the lentivirus particles. Lentiviral stocks were suspended in PBS and stored at −80° C.

Lentivirus Titration

Lentivirus titers were determined by measuring the amount of lentiviral DNA integrated into the genome of infected cells. 293T cells were plated in 24-well plates at a density of 50,000 cells/well and incubated overnight. Concentrated lentivirus stocks were added to each well together with polybrene to a concentration of 6 μg/mL. The plate was centrifuged briefly and then placed in an incubator at 37° C. with 5% CO2 for 72 hours. Genomic DNA from the lentivirus-transduced cells was extracted with a commercial kit.

Real-time quantitative PCR (RT-QPCR) was used to determine the copy number of lentiviral DNA present in the extracted genomic DNA. The albumin gene was also measured to normalize the results. The primers and probes used for RT-QPCR are shown in Table 1 below.

TABLE 1

RT-QPCR primers and probes

| Primer | Sequence (fluorescent labels) | SEQ ID NO. |
|---|---|---|
| LTR F[a] | TGACAGCCGCCTAGCATTTC | 6 |
| LTR R[a] | GCTCGATATCAGCAGTTCTTGAAG | 7 |
| LTR Probe[a] | CACGTGGCCCGAGAGCTGCATC (5'-FAM-BHQ1-3') | 8 |
| ALB F[b] | GCTGTCATCTCTTGTGGGCTGT | 9 |
| ALB R[b] | ACTCATGGGAGCTGCTGGTTC | 10 |
| ALB Probe[b] | CCTGTCATGCCCACACAAATCTCTCC (5'-FAM-BHQ1-3') | 11 |

[a]LTR = long terminal repeat. These primers specifically amplify lentiviral sequences.
[b]ALB = albumin. These primers specifically amplify the albumin gene Standard curves were constructed by amplifying known amounts of plasmid DNAs carrying the albumin or LTR gene sequences using the RT-QPCR primers described above. The copy number of lentiviral DNA in the genomic DNA was calculated as the ratio of the quantity of LTR sequences divided by the quantity of albumin sequences.

The lentivirus titer was then calculated using the following formula:

$$\text{Lentivirus titer} = \frac{\text{number of cells plated} \times \text{number of copies of lentivirus per cell}}{\text{volume of lentivirus stock added}}$$

An exemplary lentivirus preparation contained $2.6 \times 10^8$ transducing units/mL Example 2: Preparation of Anti-SSEA4 CAR T Cells T cells expressing anti-SSEA4 CAR were produced using established techniques. First, peripheral blood mononuclear cells (PBMC) were isolated from whole blood with standard blood separation tubes and the cells re-suspended in complete culture medium. T cells were isolated from the PBMC using a standard magnetic bead separation technique.

The isolated T cells were dispensed into a tissue culture plate and growth media supplemented with 200 IU/mL IL2, 10 ng/mL IL7, 5 ng/mL IL15, and 5 ng/mL IL21 was added such that the cell density was $0.5 \times 10^6$ to $1 \times 10^6$ cells/mL. The plate was incubated at 37° C. in 5% CO2 for 3 days. A lentivirus preparation produced as described above in Example 1 was added to the T cells, and polybrene was also added to a final concentration of 6 μg/ml. The plate was centrifuged at 800×g for 1 hour at room temperature, and then incubated for 5 days at 37° C. in 5% CO2. During the 5 day incubation, the T cells were maintained at a cell density of $0.5 \times 10^6$ cells/mL. The percentage of T cells expressing the anti-SSEA4 CAR was determined by fluorescence-activated cell sorting using an antibody against the EGFR domain III-IV.

In an exemplary preparation, 45.7% of T cells expressed the anti-SSEA4 CAR.

Example 3: Lysis of MCF-7 Target Cells by Anti-SSEA4 CAR T Effector Cells

The ability of anti-SSEA4 CAR T cells to lyse target cells was assessed by a co-culture assay. MCF-7 breast cancer cells, which express SSEA-4, were used as the target cells. 100 μL of MCF-7 target cells at $5 \times 10^5$ cells/mL were transferred into each well of a 96-well plate and cultured overnight at 37° C. in 5% CO2. Effector cells, i.e., anti-SSEA4 CAR T cells, untransduced T cells, and T cells transduced with a negative control lentivirus, were each suspended in serum-free RPMI1640 medium. The culture medium from the 96 well plate was removed and the target cells washed once with PBS. T cells were added into separate wells at effector to target (E/T) ratios of 1:1, 2:1, 5:1 and 10:1. The final volume of medium in each well was adjusted to 100 μL/well using RPMI1640. The co-culture was incubated for 6 h at 37° C. in 5% CO2.

A commercial kit (CytoTox 96® non-radioactive cytotoxicity assay; Promega, Wis. USA) was used to measure lysis of the target MCF-7 cells by determining the level of lactate dehydrogenase (LDH) released from these cells upon lysis. After co-culturing, the 96-well plate was centrifuged at 1200×g for 5 min. at room temperature, and 50 μL of supernatant from each well was transferred to a new 96 well plate. The LDH level in each supernatant was determined as directed by the manufacturer. Certain wells containing only target cells were treated with a lysis buffer before the centrifugation step. The supernatants from these wells were used to determine the maximum amount of LDH released by the MCF-7 cells. The results are presented in FIG. 1.

The data shows that anti-SSEA4 CAR-T cells lysed significantly more target MCF-7 cells at all E/T ratios, as compared to untransduced T cells and empty lentivirus transduced T cells.

Example 4: Cytokine Release by Anti-SSEA4 CAR-T Cells

Figure 2A:
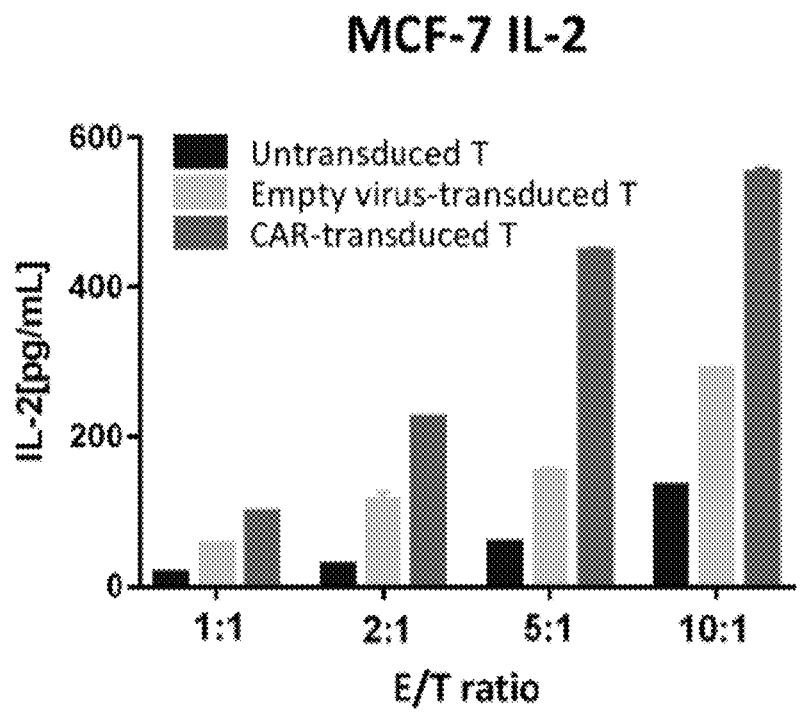
FIG. 2A is a bar graph showing the amount of IL-2 released by the indicated effector T cells after coculturing them with target MCF-7 cells at different effector to target ratios.
Figure 2B:
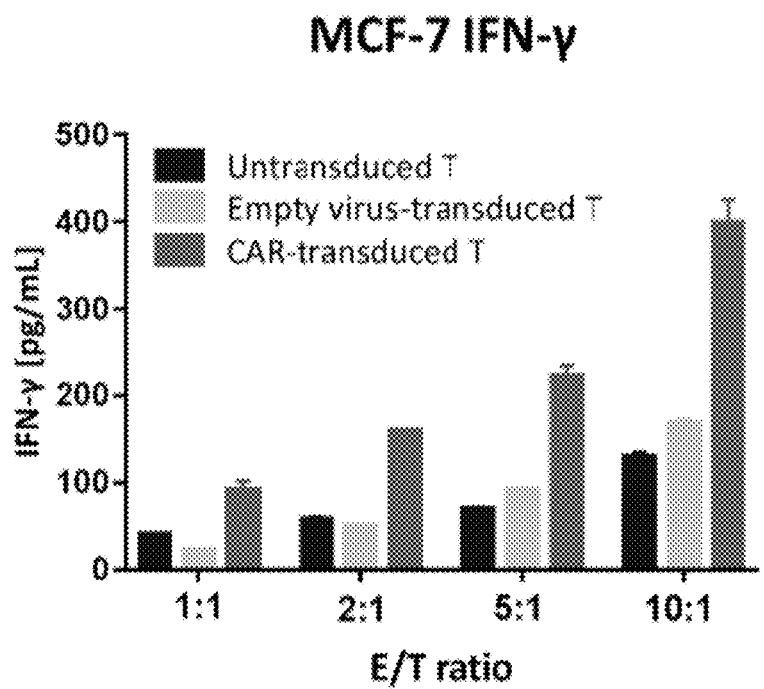
FIG. 2B is a bar graph showing the amount of IFN-γ released by the indicated effector T cells after coculturing them with target MCF-7 cells at different effector to target ratios.

The CAR-T cells described above were co-cultured with target cell line MCF7 in 96-well plates at different E/T ratio for 24 hours in RPMI1640 medium supplemented with 10% FBS in 5% CO2 at 37° C. Culture media was harvested to measure cytokine release by the CAR-T cells. Briefly, the 96-well plate was centrifuged at 1200×g for 5 min. at room temperature, after which 50 μL of supernatant from each well was transferred into a new 96 well plate. The concentration of cytokines IL-2 and IFN-γ was determined using a commercial ELISA kit according to the manufacturer's instructions. The results are shown in FIGS. 2A and 2B. The data shows that SSEA4-specific CAR-T cells robustly secreted both IL-2 and IFN-γ after engaging target tumor cells and this secretion level was significantly greater than either untransduced T cells or T cells transduced with a lentivirus lacking the CAR construct.

OTHER EMBODIMENTS

All of the features disclosed in this specification may be combined in any combination. Each feature disclosed in this specification may be replaced by an alternative feature serving the same, equivalent, or similar purpose. Unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An isolated polypeptide comprising the sequence of SEQ ID NO: 3, wherein the isolated polypeptide specifically binds to stage-specific embryonic antigen 4.

2. A chimeric antigen receptor, comprising a single chain Fv (scFv) that specifically binds to stage-specific embryonic antigen 4, and a first endodomain from CD3ζ or FcεRIγ, wherein the scFv has the sequence of SEQ ID NO: 3.

3. The chimeric antigen receptor of claim 2, further comprising a second endodomain from CD28, CD137, CD4, OX40, or ICOS, wherein the scFv is fused to the second endodomain and the second endodomain is fused to the first endodomain.

4. The chimeric antigen receptor of claim 3, wherein the chimeric antigen receptor has the sequence of SEQ ID NO: 4.

5. The chimeric antigen receptor of claim 3, further comprising an epidermal growth factor receptor t domain III-IV at its C-terminus.

6. The chimeric antigen receptor of claim 5, wherein the chimeric antigen receptor has the sequence of SEQ ID NO: 2.

* * * * *

```
SEQUENCE LISTING

<160> NUMBER OF SEQ ID NOS: 11

<210> SEQ ID NO 1
<211> LENGTH: 3972
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1354)..(3972)

<400> SEQUENCE: 1
gagtaattca tacaaaagga ctcgcccctg ccttggggaa tcccagggac cgtcgttaaa       60
ctcccactaa cgtagaaccc agagatcgct gcgttcccgc cccctcaccc gcccgctctc      120
gtcatcactg aggtggagaa gagcatgcgt gaggctccgg tgcccgtcag tgggcagagc      180
gcacatcgcc cacagtcccc gagaagttgg ggggaggggt cggcaattga accggtgcct      240
agagaaggtg gcgcggggta aactgggaaa gtgatgtcgt gtactggctc cgccttttc      300 ccgagggtgg gggagaaccg tatataagtg cagtagtcgc cgtgaacgtt cttttcgca      360 acgggtttgc cgccagaaca caggtaagtg ccgtgtgtgg ttcccgcggg cctggcctct      420
ttacgggtta tggcccttgc gtgccttgaa ttacttccac gccctggct gcagtacgtg       480 attcttgatc ccgagcttcg ggttggaagt gggtgggaga gttcgaggcc ttgcgcttaa      540
ggagcccctt cgcctcgtgc ttgagttgag gcctggcttg ggcgctgggg ccgccgcgtg      600
cgaatctggt ggcaccttcg cgcctgtctc gctgctttcg ataagtctct agccatttaa      660 aattttgat gacctgctgc gacgcttttt ttctggcaag atagtcttgt aaatgcgggc       720
caagatctgc acactggtat tcggtttt ggggccgcgg gcggcgacgg ggcccgtgcg        780
tcccagcgca catgttcggc gaggcggggc ctgcgagcgc ggccaccgag aatcggacgg      840
gggtagtctc aagctggccg gcctgctctg gtgcctggcc tcgcgccgcc gtgtatcgcc      900 ccgcctggg cggcaaggct ggcccggtcg gcaccagttg cgtgagcgga aagatggccg       960
cttcccggcc ctgctgcagg gagctcaaaa tggaggacgc ggcgctcggg agagcgggcg     1020
ggtgagtcac ccacacaaag gaaaagggcc tttccgtcct cagccgtcgc ttcatgtgac     1080
tccacggagt accgggcgcc gtccaggcac ctcgattagt tctcgagctt ttggagtacg     1140
tcgtctttag gttgggggga gggtttat gcgatggagt ttccccacac tgagtgggtg      1200
gagactgaag ttaggccagc ttggcacttg atgtaattct ccttggaatt tgcccttttt     1260
gagtttggat cttggttcat tctcaagcct cagacagtgg ttcaaagttt ttttcttcca     1320
tttcaggtgt cgtgattcga attcgccgcc acc atg gcc tta cca gtg acc gcc    1374
                                    Met Ala Leu Pro Val Thr Ala
                                     1               5 ttg ctc ctg ccg ctg gcc ttg ctg ctc cac gcc gcc agg ccg cag ctg       1422
```

```
                Leu Leu Leu Pro Leu Ala Leu Leu Leu His Ala Ala Arg Pro Gln Leu
                         10                  15                  20 caa gag tct ggc cct gga ctg gtc aag cct agc gag aca ctg agc ctg        1470
Gln Glu Ser Gly Pro Gly Leu Val Lys Pro Ser Glu Thr Leu Ser Leu
         25                  30                  35 acc tgt acc gtg tcc ggc ttt agc ctg aca agc tac ggc gtg gac tgg        1518
Thr Cys Thr Val Ser Gly Phe Ser Leu Thr Ser Tyr Gly Val Asp Trp
40                   45                  50                  55 gtc cga cag cct cct gga aaa ggc ctg gaa tgg atc ggc gtt atc tgg        1566
Val Arg Gln Pro Pro Gly Lys Gly Leu Glu Trp Ile Gly Val Ile Trp
                         60                  65                  70 ggc gga ggc agc acc aac tac aac agc gcc ctg atg agc cgg ctg acc        1614
Gly Gly Gly Ser Thr Asn Tyr Asn Ser Ala Leu Met Ser Arg Leu Thr
         75                  80                  85 atc agc aag gac aac agc aag agc cag gtg tcc ctg aag ctg agc agc        1662
Ile Ser Lys Asp Asn Ser Lys Ser Gln Val Ser Leu Lys Leu Ser Ser
                 90                  95                 100 gtg aca gcc gct gat acc gcc gtg tac tac tgt gcc aag cac gag gtg        1710
Val Thr Ala Ala Asp Thr Ala Val Tyr Tyr Cys Ala Lys His Glu Val
        105                 110                 115 ctg aga ggc tac gcc ctg gat tat tgg ggc cag ggc aca ctg gtc aca        1758
Leu Arg Gly Tyr Ala Leu Asp Tyr Trp Gly Gln Gly Thr Leu Val Thr
120                 125                 130                 135 gtg tct agc gga ggc gga gga agt ggt ggc gga gga tca ggc ggt ggt        1806
Val Ser Ser Gly Gly Gly Gly Ser Gly Gly Gly Ser Gly Gly Gly
                140                 145                 150 gga tct ctg aca cag tct ccc gct aca ctg tct ctg agc cct ggc gaa        1854
Gly Ser Leu Thr Gln Ser Pro Ala Thr Leu Ser Leu Ser Pro Gly Glu
        155                 160                 165 aga gcc aca ctg agc tgt tct gcc tct cct agc gtg tcc tac atg cac        1902
Arg Ala Thr Leu Ser Cys Ser Ala Ser Pro Ser Val Ser Tyr Met His
                170                 175                 180 tgg tat cag cag aag ccc gga cag gcc cct aga ctg ctg atc tac gac        1950
Trp Tyr Gln Gln Lys Pro Gly Gln Ala Pro Arg Leu Leu Ile Tyr Asp
185                 190                 195 acc tac aag ctg gcc tct ggc atc ccc gcc aga ttt tct ggc tct ggc        1998
Thr Tyr Lys Leu Ala Ser Gly Ile Pro Ala Arg Phe Ser Gly Ser Gly
200                 205                 210                 215 agc ggc acc gat ttc acc ctg acc ata agc agc ctg gaa cct gag gac        2046
Ser Gly Thr Asp Phe Thr Leu Thr Ile Ser Ser Leu Glu Pro Glu Asp
                220                 225                 230 ttc gct gtc tac tac tgc ttc caa ggc agc ggc ttc cct ctg aca ttt        2094
Phe Ala Val Tyr Tyr Cys Phe Gln Gly Ser Gly Phe Pro Leu Thr Phe
        235                 240                 245 gga cag ggc acc aag gtg gaa atc aag acc act acc cca gca ccg agg        2142
Gly Gln Gly Thr Lys Val Glu Ile Lys Thr Thr Thr Pro Ala Pro Arg
        250                 255                 260 cca ccc acc ccg gct cct acc atc gcc tcc cag cct ctg tcc ctg cgt        2190
Pro Pro Thr Pro Ala Pro Thr Ile Ala Ser Gln Pro Leu Ser Leu Arg
        265                 270                 275 ccg gag gca tgt aga ccc gca gct ggt ggg gcc gtg cat acc cgg ggt        2238
Pro Glu Ala Cys Arg Pro Ala Ala Gly Gly Ala Val His Thr Arg Gly
280                 285                 290                 295 ctt gac ttc gcc tgc gat atc tac att tgg gcc cct ctg gct ggt act        2286
Leu Asp Phe Ala Cys Asp Ile Tyr Ile Trp Ala Pro Leu Ala Gly Thr
                300                 305                 310 tgc ggg gtc ctg ctg ctt tca ctc gtg atc act ctt tac tgt atc tac        2334
Cys Gly Val Leu Leu Leu Ser Leu Val Ile Thr Leu Tyr Cys Ile Tyr
        315                 320                 325
```

-continued

| | |
|---|---|
| att tgg gcc cct ctg gct ggt act tgc ggg gtc ctg ctg ctt tca ctc<br>Ile Trp Ala Pro Leu Ala Gly Thr Cys Gly Val Leu Leu Leu Ser Leu<br>330                      335                      340 | 2382 |
| gtg atc act ctt tac tgt aag cgc ggt cgg aag aag ctg ctg tac atc<br>Val Ile Thr Leu Tyr Cys Lys Arg Gly Arg Lys Lys Leu Leu Tyr Ile<br>345                      350                      355 | 2430 |
| ttt aag caa ccc ttc atg agg cct gtg cag act act caa gag gag gac<br>Phe Lys Gln Pro Phe Met Arg Pro Val Gln Thr Thr Gln Glu Glu Asp<br>360                      365                      370                      375 | 2478 |
| ggc tgt tca tgc cgg ttc cca gag gag gag gaa ggc ggc tgc gaa ctg<br>Gly Cys Ser Cys Arg Phe Pro Glu Glu Glu Glu Gly Gly Cys Glu Leu<br>380                      385                      390 | 2526 |
| cgc gtg aaa ttc agc cgc agc gca gat gct cca gcc tac aag cag ggg<br>Arg Val Lys Phe Ser Arg Ser Ala Asp Ala Pro Ala Tyr Lys Gln Gly<br>395                      400                      405 | 2574 |
| cag aac cag ctc tac aac gaa ctc aat ctt ggt cgg aga gag gag tac<br>Gln Asn Gln Leu Tyr Asn Glu Leu Asn Leu Gly Arg Arg Glu Glu Tyr<br>410                      415                      420 | 2622 |
| gac gtg ctg gac aag cgg aga gga cgg gac cca gaa atg ggc ggg aag<br>Asp Val Leu Asp Lys Arg Arg Gly Arg Asp Pro Glu Met Gly Gly Lys<br>425                      430                      435 | 2670 |
| ccg cgc aga aag aat ccc caa gag ggc ctg tac aac gag ctc caa aag<br>Pro Arg Arg Lys Asn Pro Gln Glu Gly Leu Tyr Asn Glu Leu Gln Lys<br>440                      445                      450                      455 | 2718 |
| gat aag atg gca gaa gcc tat agc gag att ggt atg aaa ggg gaa cgc<br>Asp Lys Met Ala Glu Ala Tyr Ser Glu Ile Gly Met Lys Gly Glu Arg<br>460                      465                      470 | 2766 |
| aga aga ggc aaa ggc cac gac gga ctg tac cag gga ctc agc acc gcc<br>Arg Arg Gly Lys Gly His Asp Gly Leu Tyr Gln Gly Leu Ser Thr Ala<br>475                      480                      485 | 2814 |
| acc aag gac acc tat gac gct ctt cac atg cag gcc ctg ccg cct cgg<br>Thr Lys Asp Thr Tyr Asp Ala Leu His Met Gln Ala Leu Pro Pro Arg<br>490                      495                      500 | 2862 |
| gag ggc aga ggc agc ctg ctg aca tgt ggc gac gtg gaa gag aac cct<br>Glu Gly Arg Gly Ser Leu Leu Thr Cys Gly Asp Val Glu Glu Asn Pro<br>505                      510                      515 | 2910 |
| ggc ccc atg tgg ctg cag agc ctg ctg ctc ttg ggc act gtg gcc tgc<br>Gly Pro Met Trp Leu Gln Ser Leu Leu Leu Leu Gly Thr Val Ala Cys<br>520                      525                      530                      535 | 2958 |
| agc atc tct cgc aaa gtg tgt aac gga ata ggt att ggt gaa ttt aaa<br>Ser Ile Ser Arg Lys Val Cys Asn Gly Ile Gly Ile Gly Glu Phe Lys<br>540                      545                      550 | 3006 |
| gac tca ctc tcc ata aat gct acg aat att aaa cac ttc aaa aac tgc<br>Asp Ser Leu Ser Ile Asn Ala Thr Asn Ile Lys His Phe Lys Asn Cys<br>555                      560                      565 | 3054 |
| acc tcc atc agt ggc gat ctc cac atc ctg ccg gtg gca ttt agg ggt<br>Thr Ser Ile Ser Gly Asp Leu His Ile Leu Pro Val Ala Phe Arg Gly<br>570                      575                      580 | 3102 |
| gac tcc ttc aca cat act cct cct ctg gat cca cag gaa ctg gat att<br>Asp Ser Phe Thr His Thr Pro Pro Leu Asp Pro Gln Glu Leu Asp Ile<br>585                      590                      595 | 3150 |
| ctg aaa acc gta aag gaa atc aca ggg ttt ttg ctg att cag gct tgg<br>Leu Lys Thr Val Lys Glu Ile Thr Gly Phe Leu Leu Ile Gln Ala Trp<br>600                      605                      610                      615 | 3198 |
| cct gaa aac agg acg gac ctc cat gcc ttt gag aac cta gaa atc ata<br>Pro Glu Asn Arg Thr Asp Leu His Ala Phe Glu Asn Leu Glu Ile Ile<br>620                      625                      630 | 3246 |
| cgc ggc agg acc aag caa cat ggt cag ttt tct ctt gca gtc gtc agc<br>Arg Gly Arg Thr Lys Gln His Gly Gln Phe Ser Leu Ala Val Val Ser<br>635                      640                      645 | 3294 |

-continued

| | | |
|---|---|---|
| ctg aac ata aca tcc ttg gga tta cgc tcc ctc aag gag ata agt gat<br>Leu Asn Ile Thr Ser Leu Gly Leu Arg Ser Leu Lys Glu Ile Ser Asp<br>650 655 660 | | 3342 |
| gga gat gtg ata att tca gga aac aaa aat ttg tgc tat gca aat aca<br>Gly Asp Val Ile Ile Ser Gly Asn Lys Asn Leu Cys Tyr Ala Asn Thr<br>665 670 675 | | 3390 |
| ata aac tgg aaa aaa ctg ttt ggg acc tcc ggt cag aaa acc aaa att<br>Ile Asn Trp Lys Lys Leu Phe Gly Thr Ser Gly Gln Lys Thr Lys Ile<br>680 685 690 695 | | 3438 |
| ata agc aac aga ggt gaa aac agc tgc aag gcc aca ggc cag gtc tgc<br>Ile Ser Asn Arg Gly Glu Asn Ser Cys Lys Ala Thr Gly Gln Val Cys<br>700 705 710 | | 3486 |
| cat gcc ttg tgc tcc ccc gag ggc tgt tgg ggc ccg gag ccc agg gac<br>His Ala Leu Cys Ser Pro Glu Gly Cys Trp Gly Pro Glu Pro Arg Asp<br>715 720 725 | | 3534 |
| tgc gtc tct tgc cgg aat gtc agc cga ggc agg gaa tgc gtg gac aag<br>Cys Val Ser Cys Arg Asn Val Ser Arg Gly Arg Glu Cys Val Asp Lys<br>730 735 740 | | 3582 |
| tgc aac ctt ctg gag ggt gag cca agg gag ttt gtg gag aac tct gag<br>Cys Asn Leu Leu Glu Gly Glu Pro Arg Glu Phe Val Glu Asn Ser Glu<br>745 750 755 | | 3630 |
| tgc ata cag tgc cac cca gag tgc ctg cct cag gcc atg aac atc acc<br>Cys Ile Gln Cys His Pro Glu Cys Leu Pro Gln Ala Met Asn Ile Thr<br>760 765 770 775 | | 3678 |
| tgc aca gga cgg gga cca gac aac tgt atc cag tgt gcc cac tac att<br>Cys Thr Gly Arg Gly Pro Asp Asn Cys Ile Gln Cys Ala His Tyr Ile<br>780 785 790 | | 3726 |
| gac ggc ccc cac tgc gtc aag acc tgc ccg gca gga gtc atg gga gaa<br>Asp Gly Pro His Cys Val Lys Thr Cys Pro Ala Gly Val Met Gly Glu<br>795 800 805 | | 3774 |
| aac aac acc ctg gtc tgg aag tac gca gac gcc ggc cat gtg tgc cac<br>Asn Asn Thr Leu Val Trp Lys Tyr Ala Asp Ala Gly His Val Cys His<br>810 815 820 | | 3822 |
| ctg tgc cat cca aac tgc acc tac gga tgc act ggg cca ggt ctt gaa<br>Leu Cys His Pro Asn Cys Thr Tyr Gly Cys Thr Gly Pro Gly Leu Glu<br>825 830 835 | | 3870 |
| ggc tgt cca acg aat ggg cct aag atc ccg tcc atc gcc act ggg atg<br>Gly Cys Pro Thr Asn Gly Pro Lys Ile Pro Ser Ile Ala Thr Gly Met<br>840 845 850 855 | | 3918 |
| gtg ggg gcc ctc ctc ttg ctg ctg gtg gtg gcc ctg ggg atc ggc ctc<br>Val Gly Ala Leu Leu Leu Leu Leu Val Val Ala Leu Gly Ile Gly Leu<br>860 865 870 | | 3966 |
| ttc atg<br>Phe Met | | 3972 |

<210> SEQ ID NO 2
<211> LENGTH: 873
<212> TYPE: PRT
<213> ORGANISM: Artificial Sequence
<220> FEATURE:
<223> OTHER INFORMATION: Synthetic Construct

<400> SEQUENCE: 2

Met Ala Leu Pro Val Thr Ala Leu Leu Leu Pro Leu Ala Leu Leu Leu
1               5                   10                  15

His Ala Ala Arg Pro Gln Leu Gln Glu Ser Gly Pro Gly Leu Val Lys
                20                  25                  30

Pro Ser Glu Thr Leu Ser Leu Thr Cys Thr Val Ser Gly Phe Ser Leu
            35                  40                  45

```
Thr Ser Tyr Gly Val Asp Trp Val Arg Gln Pro Gly Lys Gly Leu
    50              55                  60
Glu Trp Ile Gly Val Ile Trp Gly Gly Ser Thr Asn Tyr Asn Ser
 65              70              75                  80
Ala Leu Met Ser Arg Leu Thr Ile Ser Lys Asp Asn Ser Lys Ser Gln
                85              90                  95
Val Ser Leu Lys Leu Ser Ser Val Thr Ala Ala Asp Thr Ala Val Tyr
            100             105                 110
Tyr Cys Ala Lys His Glu Val Leu Arg Gly Tyr Ala Leu Asp Tyr Trp
            115             120                 125
Gly Gln Gly Thr Leu Val Thr Val Ser Ser Gly Gly Gly Gly Ser Gly
    130             135                 140
Gly Gly Gly Ser Gly Gly Gly Gly Ser Leu Thr Gln Ser Pro Ala Thr
145             150              155                 160
Leu Ser Leu Ser Pro Gly Glu Arg Ala Thr Leu Ser Cys Ser Ala Ser
                165             170                 175
Pro Ser Val Ser Tyr Met His Trp Tyr Gln Gln Lys Pro Gly Gln Ala
            180             185                 190
Pro Arg Leu Leu Ile Tyr Asp Thr Tyr Lys Leu Ala Ser Gly Ile Pro
            195             200                 205
Ala Arg Phe Ser Gly Ser Gly Ser Gly Thr Asp Phe Thr Leu Thr Ile
    210             215                 220
Ser Ser Leu Glu Pro Glu Asp Phe Ala Val Tyr Tyr Cys Phe Gln Gly
225             230              235                 240
Ser Gly Phe Pro Leu Thr Phe Gly Gln Gly Thr Lys Val Glu Ile Lys
            245             250                 255
Thr Thr Thr Pro Ala Pro Arg Pro Pro Thr Pro Ala Pro Thr Ile Ala
            260             265                 270
Ser Gln Pro Leu Ser Leu Arg Pro Glu Ala Cys Arg Pro Ala Ala Gly
    275             280                 285
Gly Ala Val His Thr Arg Gly Leu Asp Phe Ala Cys Asp Ile Tyr Ile
    290             295                 300
Trp Ala Pro Leu Ala Gly Thr Cys Gly Val Leu Leu Leu Ser Leu Val
305             310              315                 320
Ile Thr Leu Tyr Cys Ile Tyr Ile Trp Ala Pro Leu Ala Gly Thr Cys
            325             330                 335
Gly Val Leu Leu Leu Ser Leu Val Ile Thr Leu Tyr Cys Lys Arg Gly
            340             345                 350
Arg Lys Lys Leu Leu Tyr Ile Phe Lys Gln Pro Phe Met Arg Pro Val
    355             360                 365
Gln Thr Thr Gln Glu Glu Asp Gly Cys Ser Cys Arg Phe Pro Glu Glu
    370             375                 380
Glu Glu Gly Gly Cys Glu Leu Arg Val Lys Phe Ser Arg Ser Ala Asp
385             390              395                 400
Ala Pro Ala Tyr Lys Gln Gly Gln Asn Gln Leu Tyr Asn Glu Leu Asn
            405             410                 415
Leu Gly Arg Arg Glu Glu Tyr Asp Val Leu Asp Lys Arg Arg Gly Arg
            420             425                 430
Asp Pro Glu Met Gly Gly Lys Pro Arg Arg Lys Asn Pro Gln Glu Gly
            435             440                 445
Leu Tyr Asn Glu Leu Gln Lys Asp Lys Met Ala Glu Ala Tyr Ser Glu
    450             455                 460
Ile Gly Met Lys Gly Glu Arg Arg Arg Gly Lys Gly His Asp Gly Leu
```

```
            465                 470                 475                 480
        Tyr Gln Gly Leu Ser Thr Ala Thr Lys Asp Thr Tyr Asp Ala Leu His
                        485                 490                 495
        Met Gln Ala Leu Pro Pro Arg Glu Gly Arg Gly Ser Leu Leu Thr Cys
                        500                 505                 510
        Gly Asp Val Glu Glu Asn Pro Gly Pro Met Trp Leu Gln Ser Leu Leu
                        515                 520                 525
        Leu Leu Gly Thr Val Ala Cys Ser Ile Ser Arg Lys Val Cys Asn Gly
                        530                 535                 540
        Ile Gly Ile Gly Glu Phe Lys Asp Ser Leu Ser Ile Asn Ala Thr Asn
        545                 550                 555                 560
        Ile Lys His Phe Lys Asn Cys Thr Ser Ile Ser Gly Asp Leu His Ile
                        565                 570                 575
        Leu Pro Val Ala Phe Arg Gly Asp Ser Phe Thr His Thr Pro Pro Leu
                        580                 585                 590
        Asp Pro Gln Glu Leu Asp Ile Leu Lys Thr Val Lys Glu Ile Thr Gly
                        595                 600                 605
        Phe Leu Leu Ile Gln Ala Trp Pro Glu Asn Arg Thr Asp Leu His Ala
                        610                 615                 620
        Phe Glu Asn Leu Glu Ile Ile Arg Gly Arg Thr Lys Gln His Gly Gln
        625                 630                 635                 640
        Phe Ser Leu Ala Val Val Ser Leu Asn Ile Thr Ser Leu Gly Leu Arg
                        645                 650                 655
        Ser Leu Lys Glu Ile Ser Asp Gly Asp Val Ile Ile Ser Gly Asn Lys
                        660                 665                 670
        Asn Leu Cys Tyr Ala Asn Thr Ile Asn Trp Lys Lys Leu Phe Gly Thr
                        675                 680                 685
        Ser Gly Gln Lys Thr Lys Ile Ile Ser Asn Arg Gly Glu Asn Ser Cys
                        690                 695                 700
        Lys Ala Thr Gly Gln Val Cys His Ala Leu Cys Ser Pro Glu Gly Cys
        705                 710                 715                 720
        Trp Gly Pro Glu Pro Arg Asp Cys Val Ser Cys Arg Asn Val Ser Arg
                        725                 730                 735
        Gly Arg Glu Cys Val Asp Lys Cys Asn Leu Leu Glu Gly Glu Pro Arg
                        740                 745                 750
        Glu Phe Val Glu Asn Ser Glu Cys Ile Gln Cys His Pro Glu Cys Leu
                        755                 760                 765
        Pro Gln Ala Met Asn Ile Thr Cys Thr Gly Arg Gly Pro Asp Asn Cys
                        770                 775                 780
        Ile Gln Cys Ala His Tyr Ile Asp Gly Pro His Cys Val Lys Thr Cys
        785                 790                 795                 800
        Pro Ala Gly Val Met Gly Glu Asn Asn Thr Leu Val Trp Lys Tyr Ala
                        805                 810                 815
        Asp Ala Gly His Val Cys His Leu Cys His Pro Asn Cys Thr Tyr Gly
                        820                 825                 830
        Cys Thr Gly Pro Gly Leu Glu Gly Cys Pro Thr Asn Gly Pro Lys Ile
                        835                 840                 845
        Pro Ser Ile Ala Thr Gly Met Val Gly Ala Leu Leu Leu Leu Leu Val
                        850                 855                 860
        Val Ala Leu Gly Ile Gly Leu Phe Met
        865                 870

<210> SEQ ID NO 3
```

<211> LENGTH: 235
<212> TYPE: PRT
<213> ORGANISM: Artificial Sequence
<220> FEATURE:
<223> OTHER INFORMATION: single chain Fv

<400> SEQUENCE: 3

```
Gln Leu Gln Glu Ser Gly Pro Gly Leu Val Lys Pro Ser Glu Thr Leu
1               5                   10                  15
Ser Leu Thr Cys Thr Val Ser Gly Phe Ser Leu Thr Ser Tyr Gly Val
            20                  25                  30
Asp Trp Val Arg Gln Pro Pro Gly Lys Gly Leu Glu Trp Ile Gly Val
        35                  40                  45
Ile Trp Gly Gly Gly Ser Thr Asn Tyr Asn Ser Ala Leu Met Ser Arg
50                  55                  60
Leu Thr Ile Ser Lys Asp Asn Ser Lys Ser Gln Val Ser Leu Lys Leu
65                  70                  75                  80
Ser Ser Val Thr Ala Ala Asp Thr Ala Val Tyr Tyr Cys Ala Lys His
                85                  90                  95
Glu Val Leu Arg Gly Tyr Ala Leu Asp Tyr Trp Gly Gln Gly Thr Leu
            100                 105                 110
Val Thr Val Ser Ser Gly Gly Gly Gly Ser Gly Gly Gly Gly Ser Gly
        115                 120                 125
Gly Gly Gly Ser Leu Thr Gln Ser Pro Ala Thr Leu Ser Leu Ser Pro
130                 135                 140
Gly Glu Arg Ala Thr Leu Ser Cys Ser Ala Ser Pro Ser Val Ser Tyr
145                 150                 155                 160
Met His Trp Tyr Gln Gln Lys Pro Gly Gln Ala Pro Arg Leu Leu Ile
                165                 170                 175
Tyr Asp Thr Tyr Lys Leu Ala Ser Gly Ile Pro Ala Arg Phe Ser Gly
            180                 185                 190
Ser Gly Ser Gly Thr Asp Phe Thr Leu Thr Ile Ser Ser Leu Glu Pro
        195                 200                 205
Glu Asp Phe Ala Val Tyr Tyr Cys Phe Gln Gly Ser Gly Phe Pro Leu
    210                 215                 220
Thr Phe Gly Gln Gly Thr Lys Val Glu Ile Lys
225                 230                 235
```

<210> SEQ ID NO 4
<211> LENGTH: 490
<212> TYPE: PRT
<213> ORGANISM: Artificial Sequence
<220> FEATURE:
<223> OTHER INFORMATION: Synthetic polypeptide

<400> SEQUENCE: 4

```
Met Ala Leu Pro Val Thr Ala Leu Leu Leu Pro Leu Ala Leu Leu Leu
1               5                   10                  15
His Ala Ala Arg Pro Gln Leu Gln Glu Ser Gly Pro Gly Leu Val Lys
            20                  25                  30
Pro Ser Glu Thr Leu Ser Leu Thr Cys Thr Val Ser Gly Phe Ser Leu
        35                  40                  45
Thr Ser Tyr Gly Val Asp Trp Val Arg Gln Pro Pro Gly Lys Gly Leu
    50                  55                  60
Glu Trp Ile Gly Val Ile Trp Gly Gly Gly Ser Thr Asn Tyr Asn Ser
65                  70                  75                  80
Ala Leu Met Ser Arg Leu Thr Ile Ser Lys Asp Asn Ser Lys Ser Gln
```

85                  90                  95
Val Ser Leu Lys Leu Ser Ser Val Thr Ala Ala Asp Thr Ala Val Tyr
            100                 105                 110

Tyr Cys Ala Lys His Glu Val Leu Arg Gly Tyr Ala Leu Asp Tyr Trp
            115                 120                 125

Gly Gln Gly Thr Leu Val Thr Val Ser Ser Gly Gly Gly Ser Gly
            130                 135                 140

Gly Gly Gly Ser Gly Gly Gly Ser Leu Thr Gln Ser Pro Ala Thr
145                 150                 155                 160

Leu Ser Leu Ser Pro Gly Glu Arg Ala Thr Leu Ser Cys Ser Ala Ser
                165                 170                 175

Pro Ser Val Ser Tyr Met His Trp Tyr Gln Gln Lys Pro Gly Gln Ala
                180                 185                 190

Pro Arg Leu Leu Ile Tyr Asp Thr Tyr Lys Leu Ala Ser Gly Ile Pro
            195                 200                 205

Ala Arg Phe Ser Gly Ser Gly Ser Gly Thr Asp Phe Thr Leu Thr Ile
            210                 215                 220

Ser Ser Leu Glu Pro Glu Asp Phe Ala Val Tyr Tyr Cys Phe Gln Gly
225                 230                 235                 240

Ser Gly Phe Pro Leu Thr Phe Gly Gln Gly Thr Lys Val Glu Ile Lys
                245                 250                 255

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
            275                 280                 285

Gly Ala Val His Thr Arg Gly Leu Asp Phe Ala Cys Asp Lys Arg Gly
            290                 295                 300

Arg Lys Lys Leu Leu Tyr Ile Phe Lys Gln Pro Phe Met Arg Pro Val
305                 310                 315                 320

Gln Thr Thr Gln Glu Glu Asp Gly Cys Ser Cys Arg Phe Pro Glu Glu
            325                 330                 335

Glu Glu Gly Gly Cys Glu Leu Arg Val Lys Phe Ser Arg Ser Ala Asp
            340                 345                 350

Ala Pro Ala Tyr Lys Gln Gly Gln Asn Gln Leu Tyr Asn Glu Leu Asn
            355                 360                 365

Leu Gly Arg Arg Glu Glu Tyr Asp Val Leu Asp Lys Arg Arg Gly Arg
            370                 375                 380

Asp Pro Glu Met Gly Gly Lys Pro Arg Arg Lys Asn Pro Gln Glu Gly
385                 390                 395                 400

Leu Tyr Asn Glu Leu Gln Lys Asp Lys Met Ala Glu Ala Tyr Ser Glu
                405                 410                 415

Ile Gly Met Lys Gly Glu Arg Arg Arg Gly Lys Gly His Asp Gly Leu
            420                 425                 430

Tyr Gln Gly Leu Ser Thr Ala Thr Lys Asp Thr Tyr Asp Ala Leu His
            435                 440                 445

Met Gln Ala Leu Pro Pro Arg Glu Gly Arg Gly Ser Leu Leu Thr Cys
            450                 455                 460

Gly Asp Val Glu Glu Asn Pro Gly Pro Met Trp Leu Gln Ser Leu Leu
465                 470                 475                 480

Leu Leu Gly Thr Val Ala Cys Ser Ile Ser
                485                 490

<210> SEQ ID NO 5

<211> LENGTH: 352
<212> TYPE: PRT
<213> ORGANISM: Artificial Sequence
<220> FEATURE:
<223> OTHER INFORMATION: Synthetic ploypeptide

<400> SEQUENCE: 5

```
Met Trp Leu Gln Ser Leu Leu Leu Gly Thr Val Ala Cys Ser Ile
1               5                   10                  15

Ser Arg Lys Val Cys Asn Gly Ile Gly Ile Gly Glu Phe Lys Asp Ser
            20                  25                  30

Leu Ser Ile Asn Ala Thr Asn Ile Lys His Phe Lys Asn Cys Thr Ser
        35                  40                  45

Ile Ser Gly Asp Leu His Ile Leu Pro Val Ala Phe Arg Gly Asp Ser
    50                  55                  60

Phe Thr His Thr Pro Pro Leu Asp Pro Gln Glu Leu Asp Ile Leu Lys
65                  70                  75                  80

Thr Val Lys Glu Ile Thr Gly Phe Leu Leu Ile Gln Ala Trp Pro Glu
                85                  90                  95

Asn Arg Thr Asp Leu His Ala Phe Glu Asn Leu Glu Ile Ile Arg Gly
            100                 105                 110

Arg Thr Lys Gln His Gly Gln Phe Ser Leu Ala Val Val Ser Leu Asn
        115                 120                 125

Ile Thr Ser Leu Gly Leu Arg Ser Leu Lys Glu Ile Ser Asp Gly Asp
    130                 135                 140

Val Ile Ile Ser Gly Asn Lys Asn Leu Cys Tyr Ala Asn Thr Ile Asn
145                 150                 155                 160

Trp Lys Lys Leu Phe Gly Thr Ser Gly Gln Lys Thr Lys Ile Ile Ser
                165                 170                 175

Asn Arg Gly Glu Asn Ser Cys Lys Ala Thr Gly Gln Val Cys His Ala
            180                 185                 190

Leu Cys Ser Pro Glu Gly Cys Trp Gly Pro Glu Pro Arg Asp Cys Val
        195                 200                 205

Ser Cys Arg Asn Val Ser Arg Gly Arg Glu Cys Val Asp Lys Cys Asn
    210                 215                 220

Leu Leu Glu Gly Glu Pro Arg Glu Phe Val Glu Asn Ser Glu Cys Ile
225                 230                 235                 240

Gln Cys His Pro Glu Cys Leu Pro Gln Ala Met Asn Ile Thr Cys Thr
                245                 250                 255

Gly Arg Gly Pro Asp Asn Cys Ile Gln Cys Ala His Tyr Ile Asp Gly
            260                 265                 270

Pro His Cys Val Lys Thr Cys Pro Ala Gly Val Met Gly Glu Asn Asn
        275                 280                 285

Thr Leu Val Trp Lys Tyr Ala Asp Ala Gly His Val Cys His Leu Cys
    290                 295                 300

His Pro Asn Cys Thr Tyr Gly Cys Thr Gly Pro Gly Leu Glu Gly Cys
305                 310                 315                 320

Pro Thr Asn Gly Pro Lys Ile Pro Ser Ile Ala Thr Gly Met Val Gly
                325                 330                 335

Ala Leu Leu Leu Leu Leu Val Ala Leu Gly Ile Gly Leu Phe Met
            340                 345                 350
```

<210> SEQ ID NO 6
<211> LENGTH: 20
<212> TYPE: DNA
<213> ORGANISM: Artificial Sequence

```
<220> FEATURE:
<223> OTHER INFORMATION: Synthetic primer

<400> SEQUENCE: 6
tgacagccgc ctagcatttc                                              20

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gctcgatatc agcagttctt gaag                                         24

<210> SEQ ID NO 8
<211> LENGTH: 22
<212> TYPE: DNA
<213> ORGANISM: Artificial Sequence
<220> FEATURE:
<223> OTHER INFORMATION: Synthetic probe

<400> SEQUENCE: 8
cacgtggccc gagagctgca tc                                           22

<210> SEQ ID NO 9
<211> LENGTH: 22
<212> TYPE: DNA
<213> ORGANISM: Artificial Sequence
<220> FEATURE:
<223> OTHER INFORMATION: Synthetic primer

<400> SEQUENCE: 9
gctgtcatct cttgtgggct gt                                           22

<210> SEQ ID NO 10
<211> LENGTH: 21
<212> TYPE: DNA
<213> ORGANISM: Artificial Sequence
<220> FEATURE:
<223> OTHER INFORMATION: Synthetic primer

<400> SEQUENCE: 10
actcatggga gctgctggtt c                                            21

<210> SEQ ID NO 11
<211> LENGTH: 26
<212> TYPE: DNA
<213> ORGANISM: Artificial Sequence
<220> FEATURE:
<223> OTHER INFORMATION: Synthetic probe

<400> SEQUENCE: 11
cctgtcatgc ccacacaaat ctctcc                                       26
```